US00PP24027P2

(12) United States Plant Patent
van Noort

(10) Patent No.: US PP24,027 P2
(45) Date of Patent: Nov. 12, 2013

(54) ***GERANIUM* PLANT NAMED 'RISE AND SHINE'**

(50) Latin Name: *Geranium wallichianum*
Varietal Denomination: Rise and Shine

(76) Inventor: Marco van Noort, Warmond (NL)

( * ) Notice: Subject to any disclaimer, the term of this patent is extended or adjusted under 35 U.S.C. 154(b) by 128 days.

(21) Appl. No.: 13/385,253

(22) Filed: Feb. 10, 2012

(51) Int. Cl.
*A01H 5/00* (2006.01)

(52) U.S. Cl.
USPC ..... Plt./324

(58) Field of Classification Search
USPC ..... Plt./324
See application file for complete search history.

*Primary Examiner* — June Hwu
(74) *Attorney, Agent, or Firm* — Penny J. Aguirre

(57) ABSTRACT

A new cultivar of *Geranium wallichianum*, 'Rise and Shine', characterized by its large flowers that are tri-color with purple veins; pale purple centers become purple-violet in the middle regions and purple on the outer regions, and by its lack of seed production.

2 Drawing Sheets

Botanical classification: *Geranium wallichianum.*
Cultivar designation: 'Rise and Shine'.

BACKGROUND OF THE INVENTION

The present invention relates to a new and distinct cultivar of *Geranium* plant, botanically known as *Geranium wallichianum* 'Rise and Shine' and will be referred to hereafter by its cultivar name, 'Rise and Shine'.

'Rise and Shine' was derived from a breeding project in Warmond, The Netherlands. The inventor's goal was to develop new cultivars of *Geranium wallichianum* that are long blooming, free of disease, and exhibit unique flower coloration. 'Rise and Shine' was selected in 2007 as a single unique plant from among the seedlings that resulted from a cross made between unnamed plants from the Inventor's breeding program of *Geranium wallichianum.*

Asexual reproduction of the new cultivar was first accomplished by division by the Inventor in Warmond, The Netherlands in summer of 2007. Propagation by tissue culture and division has determined that the characteristics of this cultivar are stable and are reproduced true to type in successive generations.

SUMMARY OF THE INVENTION

The following traits have been repeatedly observed and represent the characteristics of 'Rise and Shine'. These attributes in combination distinguish 'Rise and Shine' as a new and distinct cultivar of *Geranium.*

1. 'Rise and Shine' exhibits flowers that are tri-color with purple veins; pale purple centers, purple-violet in the middle region and purple on the outer region.
2. 'Rise and Shine' exhibits flowers that are large in size (an average of 4 cm in diameter).
3. 'Rise and Shine' is sterile and does not produce seed.

The new cultivar, 'Rise and Shine', is unique from the all other cultivars of *Geranium wallichianum* known to the Inventor. The parent plants of 'Rise and Shine' both differ from 'Rise and Shine' in having smaller flowers and in producing seeds. 'Rise and Shine' can be compared to *Geranium wallichianum* cultivars 'Buxton's Variety' (not patented) and 'Sweet Heidy' (U.S. Plant Pat. No. 19,533). 'Buxton's Variety' differs from 'Rise and Shine' in having smaller flowers with dark centers and in producing seed. 'Sweet Heidy' differs from 'Rise and Shine' in having slightly smaller flowers and in producing seed.

BRIEF DESCRIPTION OF THE DRAWING

The accompanying colored photographs illustrate the overall appearance and distinct characteristics of the new *Geranium*. The photographs were taken of three year-old plants of 'Rise and Shine' as grown outdoors in a garden in Warmond, The Netherlands.

The photograph in FIG. 1 provides an overall view of a plant of 'Rise and Shine' in bloom.

Figure 1:
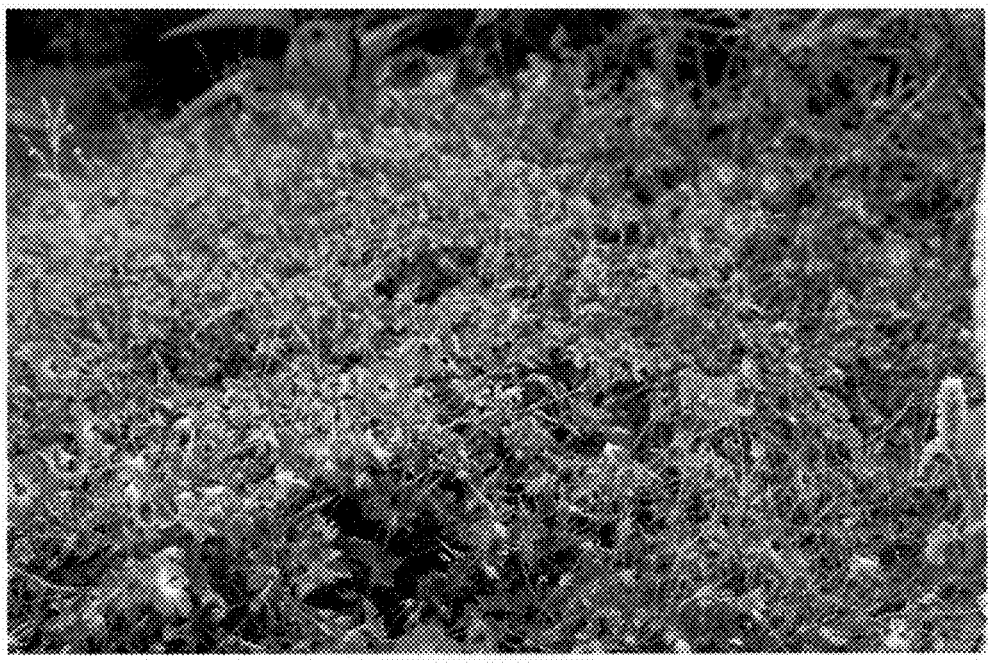
Figure 2:
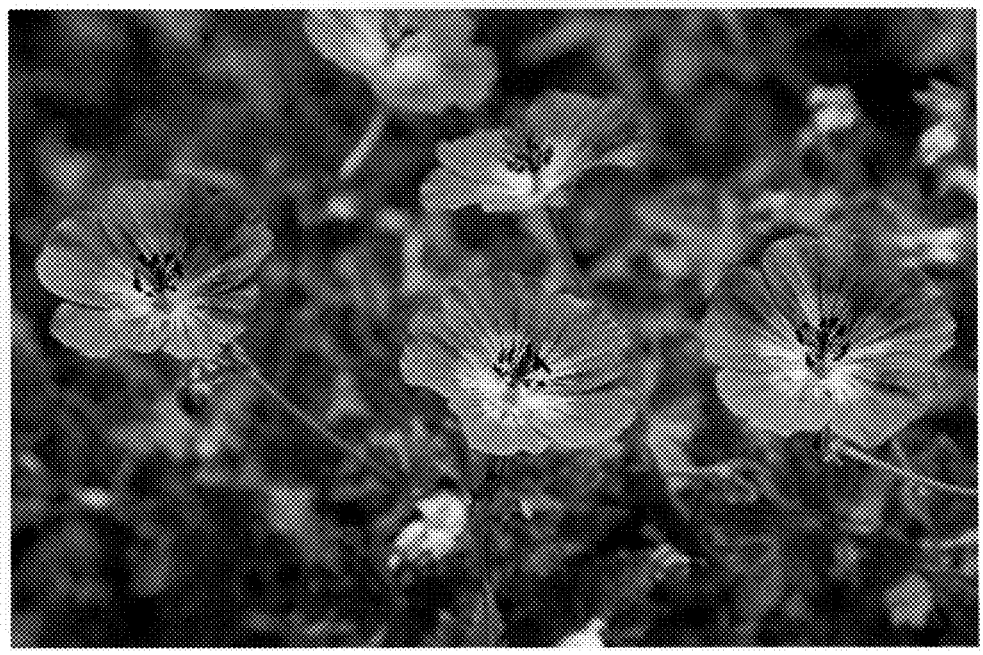

The photograph in FIG. 2 provides a close-up view of the flowers of 'Rise and Shine'.

The colors in the photographs are as close as possible with the photographic and printing technology utilized. The color values cited in the detailed botanical description accurately describe the colors of the new *Geranium.*

DETAILED BOTANICAL DESCRIPTION OF THE PLANT

The following is a detailed description of 1 year-old, field grown plants of the new cultivar as grown outdoors in Warmond, The Netherlands with average day temperatures of 14° C. to 30° C. and average night temperatures of 6° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Late spring to late summer in The Netherlands.

*Plant habit.*—Herbaceous perennial with broad spreading growth habit.

*Height and spread.*—Reaches 20 cm in height and about 65 cm in spread.

*Cold hardiness.*—At least to U.S.D.A. Zone 5.

*Heat tolerance.*—At least tolerant to temperature up to 35° C.

*Diseases and pests.*—Not more susceptible to pests and diseases than other varieties of *Geranium.*

*Root description.*—Fleshy roots extending from stout rootstock.

*Growth rate.*—Moderate to highly vigorous, about 15 cm per month in spring.

*Propagation.*—Division and In vitro propagation.

Stem description:

*Stem size.*—Average of 20.6 cm in length and 2.5 mm in width.

*Stem shape.*—Round.

*Stem color.*—183A to 183B.

*Stem surface.*—Slightly glossy with stems moderately covered with short soft hairs; average of 0.7 mm in length, 157D in color.

*Internode length.*—Average of 5.5 cm.

*Branching.*—Moderately branched with an average of 6 lateral branches.

Foliage description:

*Leaf shape.*—Orbicular (overall shape), palmately cleft with an average of five lobes.

*Leaf division.*—Simple.

*Leaf base.*—Hastate (not overlapping).

*Leaf apex.*—Acute.

*Leaf venation.*—Palmate, 144A in color on upper surface and 138B on lower surface, main and secondary veins on lower surface densely covered with short pubescent hairs, average length 1 mm, hairs on both sides are a blend of N155A and 157D.

*Leaf margins.*—Palmately cleft into an average of five lobes, margins of lobes serrate.

*Leaf attachment.*—Petiolate.

*Leaf arrangement.*—Opposite.

*Leaf surface.*—Dull, moderately dense pubescence on upper and lower surface with short hairs; average of 0.5 mm in length, a blend of N155A and N157D in color.

*Leaf color.*—Young leaves upper surface; 143A, young leaves lower surface; 144A, mature leaves upper surface; N137A to N137B, mature leaves lower surface; 138B.

*Leaf size.*—Average of 5.0 cm in length and 6.1 cm in width.

*Leaf quantity.*—Average of 8 leaves per lateral branch.

*Petioles.*—Average of 4.2 in length and 2 mm in diameter, color: upper surface; a blend of 178A and 183A, lower surface; 152C to 152D.

*Stipules.*—1 per leaf at the base of the basal leaves, broadly ovate, average of 1.7 cm in length, average of 1.3 cm in width, color: young upper and lower surfaces; 144B to 144C in color with margins 187C to 187D in color, mature upper and lower surfaces; 144B to 144C.

Flower description:

*Inflorescence type.*—Single, rotate flowers, arranged in pairs.

*Lastingness of flowers.*—About 7 days on the plant, sepals persistent.

*Flower size.*—Average of 1.0 cm in height and 4.0 cm in diameter.

*Flower fragrance.*—None.

*Flower number.*—Average of 2 per lateral system.

*Flower aspect.*—Upright to slightly outward.

*Flower buds.*—Elliptic in shape, average of 1.3 cm in length and up to 6 mm in diameter, 138A in color, surface densely covered with short pubescent hairs 1 mm in length and N155A in color.

*Corolla features.*—Petals are unfused and arranged in a rotate form, slightly cupped.

*Petal number.*—5.

*Petal shape.*—Obcordate.

*Petal color.*—Opening upper surface; N80A with top ⅓ region N88B, base region ranging from 76A to 76C, and veins N79C to N79D, opening lower surface; N81C, veins N79B, fully open upper surface; N80A with top ⅓ region N88B, base region ranging from 76A to 76C, and veins N79C to N79D, fully open lower surface; N81C, base and veins N79B, fading to; N81B, base 76A to 76C, veins N79C to N79D.

*Petal surface.*—Velvety, very slightly glossy on upper and lower surface.

*Petal margins.*—Entire.

*Petal apex.*—Straight, obtuse to slightly retuse.

*Petal size.*—Average of 2.1 cm in length and 1.6 cm in width.

*Calyx form.*—Rotate and slightly cupped.

*Sepals.*—5, oblong to elliptic in shape, average of 1.5 cm length and 4.5 mm in width, entire margin, mucronate apex, cuneate base, dull surface, color young upper surface; 138A, color young lower surface; 138A to 138B, mature upper surface 143A to 143B, mature lower surface; 143B.

*Peduncles.*—Round in shape, average of 7.3 cm in length and 2 mm in diameter, moderately strong, held at about a 45° angle, varying between 30° and 60°, color: upper surface; blend of 178A and 183A, lower surface 152C to 152D.

*Pedicels.*—Round in shape, average of 4.8 cm in length and 1 mm in diameter, moderately strong, held at about a 15° angle, color: upper surface; a blend of 178A and 183A, lower surface; 152C to 152D.

Reproductive organs:

*Gynoecium.*—1 pistil, about 1.1 cm in length, 5 stigmas are decurrent and N186C in color, style is about 7 mm in length and 145A in color, ovary is 145B to 145C in color.

*Androcoecium.*—10 stamens, anthers are dorsifixed and oblong in shape, 3 mm in length, and 203C in color, filaments are 7 mm in length and N187D in color with base 145D, pollen is low in quantity and 198C to 198D in color. Fruit/Seeds. — Sterile, seeds are not produced.

It is claimed:

1. A new and distinct cultivar of *Geranium* plant named 'Rise and Shine' as herein illustrated and described.

* * * * *